US006274566B1

(12) United States Patent
Eliaz et al.

(10) Patent No.: US 6,274,566 B1
(45) Date of Patent: Aug. 14, 2001

(54) METHODS FOR TREATING MAMMALS WITH MODIFIED ALGINATES AND PECTINS

(75) Inventors: Isaac Eliaz, San Rafael; Michael McCulloch, San Anselmo, both of CA (US)

(73) Assignee: Econugenics, Inc., San Rafael, CA (US)

( * ) Notice: Subject to any disclaimer, the term of this patent is extended or adjusted under 35 U.S.C. 154(b) by 0 days.

(21) Appl. No.: 09/255,265

(22) Filed: Feb. 23, 1999

(51) Int. Cl.[7] .................. A61K 31/732; A61K 31/734
(52) U.S. Cl. ............................................... 514/54
(58) Field of Search .................................. 514/54

(56) References Cited

FOREIGN PATENT DOCUMENTS

61064701 * 9/1993 (JP) .
09235234 * 9/1997 (JP) .

OTHER PUBLICATIONS

Kimura et al., J. Ethnopharmacol., 54(1), 47–54 (abstract), Oct. 1996.*
Pienta et al., Journal of the National Cancer Institute, 87(5), pp. 348–353, Mar. 1, 1995.*
Pharmaceutical Evulation of Ibuprofen Fast–Absorbed Syrup Containing Low Molecular–weight Gelatin, J. Pharm Sci. 1992, Feb; 81(2):141–4, S. Kimura, et al. (abstract).
Chitosans as Absorption Enhancers for Poorly Absorbable Drugs. 1: Influence of Molecular Weight and Degree of Acetylation on Drug Transport Across Human Intestinal Epithelial (Caco–2) Cells; Pharm Res. 1996 Nov;13(11):1686–92, N.G. Schipper, et al. (Abstract).
Validation of Polyethylene Glycol 3350 as a Poorly Absorable Marker for Intestinal Perfusion STudies; Dig. Dis. Sci. 1997 Jan; 42(1):1–5; L.R. Schiller, et al. (abstract).
Absorption Enhancement in Intestinal Epithelial Caco=2 Monolayers by Sodium Captrate: Assessment of Molecular Weight Dependence and Demonstration of Transport Routes; J. Drug Target 1998; 5(3):215–23; T. Lindmark, et al. (abstract).
Deletion of algK in Mucoid Pseudomonas Aeruginosa Blocks Alignate Polymer Formation and REsults in Uronic Acid Secretion, J. Bac., Feb., 1998, p. 634–641; Sumita Jain, et al. (abstract).
Microbial Enzymes and Their Application to Pharmaceutical Areas; Department eof Food Safety and Utilization, Nov. 24, 1998 19:32–46, Murata Kousaku, et al.
Algin; Chapter 6, pp. 105–143; Kenneth Clare, et al. (1993).
Adsorption of Charged Drugs to Oppositively Charged Polysaccharides—A Study of the Influence of Polysaccharide Structure and Hydrophobicity of the Drug Molecules; Nov. 24, 1998; Fredrick, Hed at al., on–line at http://www.geocities.com/hotsprings/1851/paper.htm.

* cited by examiner

Primary Examiner—Phyllis G. Spivack
(74) Attorney, Agent, or Firm—Piper, Marbury, Rudnick & Wolfe, LLP; Steven B. Kelber

(57) ABSTRACT

A method for binding tumor emboli circulating in the blood of mammals is provided by oral or intravenous administration of a modified alginate, prepared from alginic acid by thermal degradation/hydrolysis or enzymatic degradation. The modified alginate has a molecular weight of no more than 40,000 daltons, and is water soluble.

6 Claims, No Drawings

METHODS FOR TREATING MAMMALS WITH MODIFIED ALGINATES AND PECTINS

BACKGROUND OF THE INVENTION

Field of the Invention

This invention pertains to compositions, and methods of using the same, to protect mammals from, and treat mammals with diseases and conditions, mediated by various agents, including disease agents, heavy metals and other substances that can be bound by surface interaction with low molecule weight pectinates and alginates.

It is well known that gelling agents may be effective in binding to a variety of substances, in vitro. While high molecular weight binding substances are known, it is difficult for such substances to pass various blood barriers, including the gut, and circulate freely in the bloodstream. Their solubility in water is generally too low to permit in vivo utility of any kind.

Cancer metastasis is a stage of cancer which frequently marks conversion to an incurable disease. Most cancers share the ability to metastasize. This application has applicability to all metastatic cancers. In the metastatic process, cells depart from the primary tumor, invade the basement membrane, traverse the bloodstream as tumor cell emboli and interact with the vascular endothelium of the target organ. There, they proliferate to form secondary colonies. Kohn, Anti-Cancer Res., 13:2553–2259 (1993). It has been demonstrated that modified citrus pectin, administered orally, may be effective in suppressing or preventing metastases, by binding to residues on the cell surface, presumably through galactosyl residues in the modified (low molecular weight) pectin, perhaps through surface galectin-3. Pienta, et al., J. Nat. Cancer Inst. 87, 348–353 (1995).

Cancer is not the only inimical element circulating in mammalian blood streams, however, and in many cases, cancer is mediated by inorganic agents present. Thus, heavy metals and minerals, such as calcium, can induce arteriosclerosis, which is also influenced by the presence of cholesterol in the bloodstream. While there are a variety of treatments for elements such as heavy metals, typically, these embrace removal of portions of the blood supply, and treatment of the same.

Pectin, or pectinates, digestion products of pectin, are generically known as gelling agents, as are alginates. Alginates occur naturally, and a chief source is seaweeds. Alginates are formed by a mixture of polymannuronic acid and polyguluronic acid. Repeating sub-units are bound by glycosidic links at the 1a-4a-di-axial position (polyguluronic acid) while repeating sub-units of polymannuronic acid are bound by galactic links at the 1e-4e di-equatorial position. Like pectins, naturally occurring algins are high molecular weight products. They can, however, be reduced to low molecular weight products (defined herein as 40,000 daltons or less) by either chemical treatment (alkaline hydrolysis) or enzymatic degradation. Alginates generally have superior protein recovery rates when compared to pectinates of relatively similar molecular weight. Clare, Industrial Gums (1993 $3^{rd}$ Edition) and therefor exhibit a stronger ability than pectinates to bind with galectin 3, the carbohydrate binding protein on the surface of cancer cells.

A wide variety of seaweeds, which include algins, as well as the alginic constituent components, have been used in studies treating cancer. See, e.g., Itoh, Anti-Cancer Res. Sept.–Oct. (1995) and Kitasato, Archives of Exp. Med., 1987. In general, these studies and recommendations focus on various polysaccharide constituents such as fucoidan, which exhibits anti-tumor activity, but do not report the utility of alginates in preventing cell adhesion, or otherwise suppressing metastatic events. Low molecular weight alginates have been associated with the reduction of cholesterol in softdrinks, and alginate-coated sheets have been employed for the manufacture of a prototype artificial pancreas. Islet Medical, Feb., 1998. Transplants coated with alginates have also been used in the treatment of diabetes. There does not appear to be a report, however, of the use of low molecular weight alginates as opposed to pectins in the prevention or treatment of metastasis. Because of the superior recovery rate associated with alginates, it would be of value to be able to use alginates for this purpose.

Besides binding cancer cells, alginates are known to be effective metal binding compounds.

Accordingly, it remains an object of those of skill in the art to establish a method by which cancer metastasis can be prevented or reduced. It is also a goal of those of skill in the art to obtain a method for the treatment and/or removal of heavy metals, radioactive products and the like, without removal of part or all of the blood supply of a patient. It is an additional object of those of skill in the art to find a safe and effective treatment for high circulating values of calcium and other minerals which contribute calcium deposits such as calcinosis (large calcium deposits present in autoimmune condition like dermatomiositis) as well as treating atherosclerosis. A further object of those of skill in the art is to provide a method for treating arteriosclerosis with reduced side effects.

SUMMARY OF THE INVENTION

The above objects, and other objects that are made clear by the discussion below, are met by the oral or intravenous administration of modified alginates, modified pectins, or a combination of both, alone or together with promoter compounds.

For the treatment or prevention of metastases, modified alginates (herein, modified alginates and modified pectinates refer to low molecular weight products, no more than 40,000 daltons, obtained by hydrolysis or digestion of algin or pectin). Alginates may be distinguished from pectinates which have galactose residues known to show high affinity for galectins (a carbohydrate binding protein) which are exhibited on the surface of cell emboli.

In addition to the treatment of metastatic cancer, low molecular weight algins and low molecular weight pectins can be used in chelation therapy, that is, administration to bind heavy metals, toxins and calcium. While these potential poisons (including mercury, lead, arsenic, radioactive materials and others) can be chelated in the intestine, the method is also effective to chelate heavy metals circulating in the bloodstream. The chelation of calcium, as well as cholesterol binding, is effective in the treatment of arteriosclerosis. Methods for modifying pectins to obtain low molecular weight pectinates are known to those of skill in the art and can be obtained from commercial sources. See, e.g., Pienta, et al. Modified alginates are produced by a similar method, either through alkaline hydrolysis or enzymatic degradation using alginate lyase. The final modified alginate or pectinate must be water soluble, and of a molecular weight of 40,000 daltons or below. It may be combined with pharmaceutically acceptable carriers suitable for oral or intravenous administration, depending on the treatment method desired. Dosage levels will vary from 5–1500 mg per kg of body weight, per day, and may be sustained over a prolonged period. A preferred range may be 10 mg/kg/day to 1,000 mg/kg/day.

DETAILED DESCRIPTION OF THE INVENTION

For the treatment or prevention of cancer metastases, modified alginates (MA) are used, either alone, or in combination with modified pectinates. In other methods of treatment described herein, modified alginates or modified pectinates, or their combination, may be effectively used.

A water soluble, low molecular weight MA is prepared from alginic acid. An aqueous suspension is prepared, and the pH is adjusted to 10.0 with the addition of a hydroxide, suitably sodium hydroxide, for 30 minutes. This is followed by a reduction to 3.0 by the addition of HCl, according to the method of Albersheim. et al., Arch. Biochem. Biophys. 90:46–49 (1960). pH modification is conducted at temperatures of 85–95° C. for a period of up to 24–48 hours. After thermal degradation over an interval lasting 8–48 hours, sodium hydroxide and/or potassium hydroxide are added to equilibrate the MA at approximately 6.0–6.5. The process may be monitored throughout the thermal degradation stage, to evaluate molecular weight. The essential characteristics of the inventive MA is that it be water soluble, and of a molecular weight below 40,000 daltons. This is necessary to ensure adequate passage to the blood during digestion. The MA may be dried by drum or spray drying.

In an alternate process, the alginic acid is degraded enzymatically, rather than thermally. In this process, an aqueous preparation of alginic acid is modified to a pH of 3.0–6.0, with an optimum value of about 4.5, using a mixture of sodium and potassium hydroxide. The concentration of alginic acid in the aqueous preparation for both thermal and enzymatic degradation is approximately 10–30%. In the enzymatic degradation, the temperature for maximum enzymatic activity is 30–40° C., and is maintained over a period of 5–7 days. As the case with thermal degradation, the enzymatic degradation process can be monitored to evaluate the molecular weight. (Molecular weight herein is weight average molecular weight). pH is adjusted to a value of 6.0–6.5, and the solution dried by drum or spray drying.

A principle method of using the MA of the invention is in the prevention or treatment of cancer metastasis. Because the individual units of modified alginates, guluronic acid and mannuronic acid, can be linked and cross-linked in a variety of different fashions (and obtained that way from a variety of different seaweeds) the resulting units, which are bound by galectin receptors on the surface of tumor cell emboli, can be presented in a variety of concentrations and accessibilities. Preferably, a large variety of MA is employed, to maximize the likelihood that effective binding between the MA and potential metastatic cell tumors, mobilized in the bloodstream, can be achieved. While no MA is known to be cancer specific, it is believed that certain MA configurations, including reduced cross-linking, and a high degree of alternating monomers may result in the exposure of greater binding units, providing for greater effectiveness.

The MA of this invention may be combined with modified pectin, which, as discussed above, has previously been shown to be at least of limited effectiveness in preventing or reducing cancer metastasis.

In this method of the invention, patients at risk, including humans, receive the MA, alone, or together with modified pectin (MP) (also of molecular weight below 40,000 daltons) alone, or together with agents which enhance binding, such as whey protein (rich in glutathione), selenium and related binding adjuvants. Additional effective agents are those which aid excretion through both the kidneys and intestines, such as diuretics, phase two initiators such as sulfured amino acids, EDTA, etc.

The patient receives the MA either orally or intravenously. Alginates have been shown to be well tolerated through both methods of administration. In oral administration, a daily dosage of about 15 grams is believed to be effective, but dosages can vary from 5 mg per kg of body weight on up to 1,000–1,500 mg of MA per kg of body weight, and more, per day. It will be recognized that cancer metastasis is an ongoing process, and that the MA of the invention is administered over a sustained time period, while the primary tumor is treated with conventional antineoplastic remedies. Once treatment of the primary tumor has been successful, the administration of MA continues for an extended period, to ensure surviving tumor cell emboli, mobilized but not yet at the bloodstream at the time of termination of primary tumor treatment, are bound and metastatic cancer suppressed. Dosage values after the first year of administration may be reduced from initial higher levels.

Neither MA or MP is known to have any side effects, or exhibit cytopathology or toxicology. Oral administration can be a reconstitution of dried MA in water or other suitable solution, or using a wide variety of conventional excipients, vehicles, flavorings and the like. Controlled dosage formulations are preferred to ensure adequate medication over time.

In the alternative, patients for whom oral administration is either not suitable or not available can receive the MA, in a pharmaceutically acceptable carrier in an amount sufficient to provide the effective daily dose intravenously (IV), as discussed above.

In this respect, the administration of MA may be doubly effective in the treatment of cancer and other diseases characterized by an inadequate immune response. As noted previously, the MA of the invention is comprised of guluronic and mannuronic acid monomers. Unbound mannuronic acid is broken down by the body to uronic acid and mannose. It is known that the administration of mannose stimulates the immune system. Turner, Scand. J. Immunol. 48(2):124–126 (1998); Kakkanaiah, et al., Clin. Diagn. Lab Immunol. 5 (3):319–321 (1998). To achieve significant immune stimulation, MA levels should be on the order of 10–15 grams/day.

In another embodiment of the invention, MA and/or MP are administered to chelate poisonous metals, including mercury, lead, nickel and others, that may be circulating in the blood. Blood poisoning due to the presence of heavy metals and related toxins can be treated by administration of MP and/or MA to bind the discreet metal particles. In this respect, MP and MA are gelling agents, and the bound particles/gel are safely removed by the body. Dosage levels for this type of treatment tend to be lower, on the order of 50–1,000 mg/kg body weight. It should be noted that many poisonous metals enter the bloodstream through accidental or unintentional ingestion, pollution and ingestion of amalgam from silver fillings and other metals during dental work and from leakage and oral administration of MA and MP in this method effectively isolates and removes dangerous metals whether present intestinally, or in the bloodstream. Metals which are recognized toxins, and frequently concentrated by plants and animals that constitute part of the food chain, or otherwise are present in the environment, such as mercury, arsenic, cadmium and lead, may be effectively treated by this method.

The binding of MP and MA to calcium has been extensively studied. Additionally, MA and MP exhibit the ability to bind cholesterol. Effective binding of circulating calcium (although not all calcium) and cholesterol is an effective method of treating and/or preventing arteriosclerosis. This invention is distinguished in that, by using low molecular weight MA and /or MP readily passed to the bloodstream, binding of cholesterol and calcium beyond the intestines can be achieved. By binding these compositions, deposit of plaques on the endothelial walls is prevented, thus providing an effective method of treating arteriosclerosis and related conditions, including hypertension, coronary heart disease and related condition is provided, without significant side effects. In the prevention or treatment of target individuals who may be at risk of developing severe arteriosclerosis, or being treated for the same, dosage values of 2–15 grams per day, or in the range of 150 mg/kg body weight are appropriate.

This invention has been described by both specific example, and generic description. Alternatives, particularly alternatives with respect to the composition and characteristics of MA and MP, as well as treatment regiment, will occur to those of ordinary skill in the art, without the exercise of inventive faculty. Such alternatives remain within the scope of the invention, unless specifically excluded by the recitation of the claims set forth below.

What is claimed is:

1. A method of binding tumor emboli circulating in the bloodstream of a mammal, comprising administering to said mammal an amount of modified alginate having a molecular weight of no more than 40,000 daltons in an amount sufficient to provide a concentration of modified alginate in said bloodstream sufficient to bind said tumor emboli, wherein said modified alginate is obtained by hydrolysis or enzymatic degradation of alginic acid.

2. The method of claim 1, wherein said administration of modified alginate is accompanied by administration of modified pectin having a molecular weight of no more than 40,000 daltons, and wherein said modified pectin is obtained by hydrolysis or enzymatic degradation of pectin.

3. The method of claim 1, wherein said administration is intravenous.

4. The method of claim 1, wherein said administration is oral.

5. The method of claim 2, wherein said administration is intravenous.

6. The method of claim 2, wherein said administration is oral.

\* \* \* \* \*